United States Patent [19]

Barry

[11] 4,050,100
[45] Sept. 27, 1977

[54] PERMANENTLY IMPLANTED HAIR PIECE ATTACHING MEANS

[76] Inventor: Robert J. Barry, 76 Cedargrove Road, Little Falls, N.J. 07424

[21] Appl. No.: 685,650

[22] Filed: May 12, 1976

[51] Int. Cl.² .................. A61F 1/00; A61B 17/00
[52] U.S. Cl. .................................. 3/1; 128/330
[58] Field of Search ........................ 3/1; 128/330

[56] References Cited

U.S. PATENT DOCUMENTS

| 3,608,095 | 9/1971 | Barry | 128/330 |
|---|---|---|---|
| 3,811,425 | 5/1974 | Widdifield | 3/1 X |
| 3,858,247 | 1/1975 | Bauman | 128/330 X |
| 3,862,453 | 1/1975 | Widdifield | 3/1 |
| 3,914,801 | 10/1975 | Dick et al. | 3/1 |

*Primary Examiner*—Channing L. Pace
*Attorney, Agent, or Firm*—B. P. Fishburne, Jr.

[57] ABSTRACT

A straight needle for penetrating the scalp substantially parallel to the underlying bone structure has a trailing tissue-compatible flexible preferably transparent plastic tube which contains a stainless steel bushing. After being pulled through the scalp puncture openings by the needle, the needle with a portion of the trailing tube is severed and discarded with a section of the tube and the contained bushing remaining in the scalp with end portions projecting outwardly of the puncture openings. The external end portions of the bushing are turned upwardly approximately normal to the scalp and a parallel lock bar to which a hair piece may be anchored is attached in close parallel relationship to the implanted bushing by a wire which is threaded through the bushing and its encasing tube before bending the ends of the bushing. The wire ends are also threaded through the tubular lock bar and tightened prior to crimping the ends of the lock bar on the wire and removal of excess wire ends to complete the implanted unit. Sterile packaging is featured. Only simple tools are required. Strain on the edges of scalp puncture openings is eliminated. By a modification, plural bushings can be implanted in the scalp in a connected array by continuous crimped wires which will prevent both the wires and the bushings from moving relatively. The wire crimped portions between bushings lie close to the scalp for the attachment of a hair piece.

7 Claims, 20 Drawing Figures

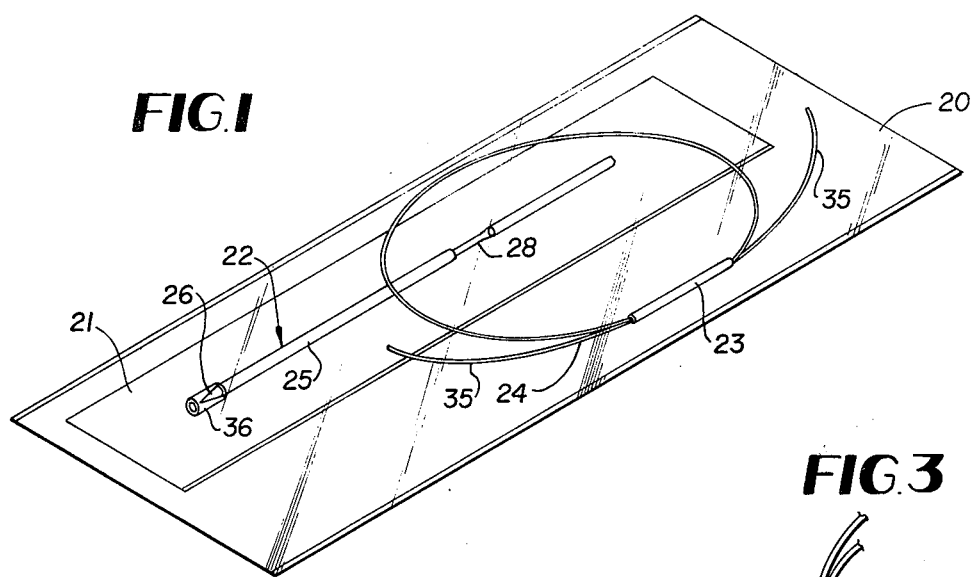
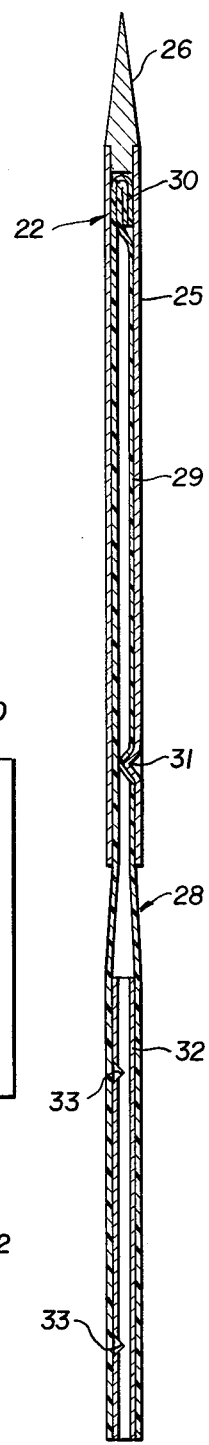
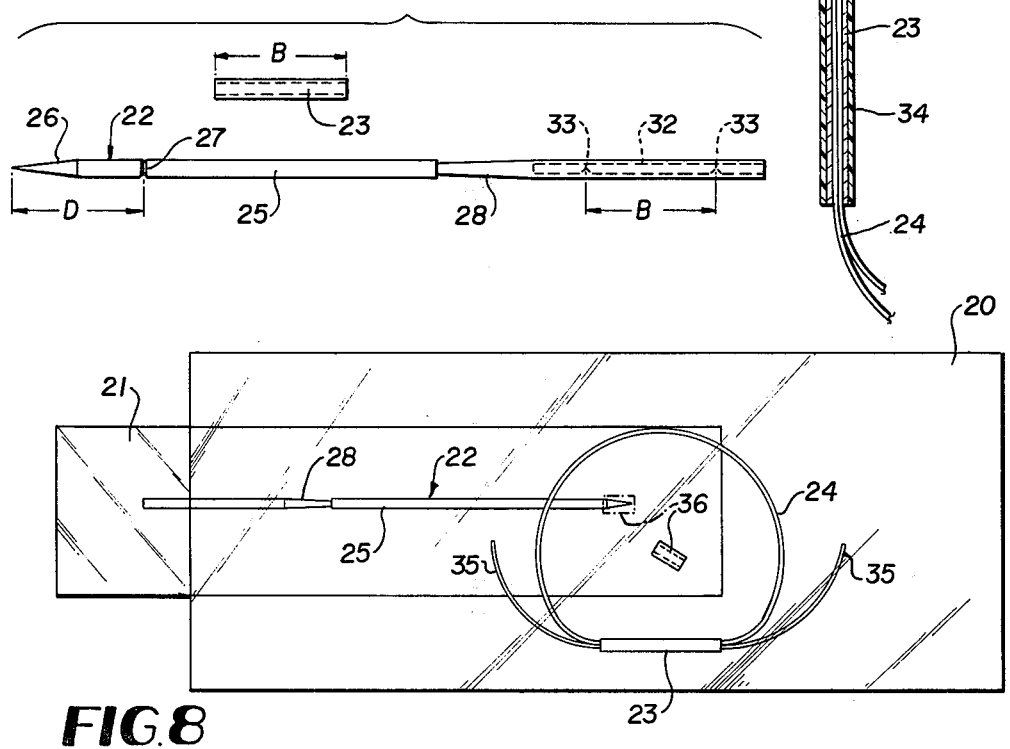
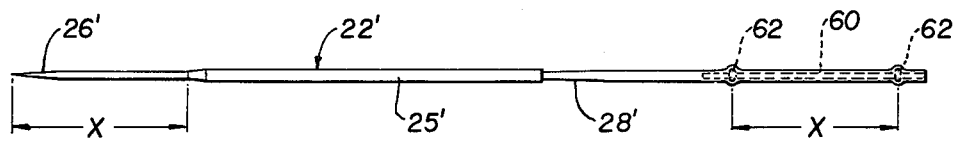

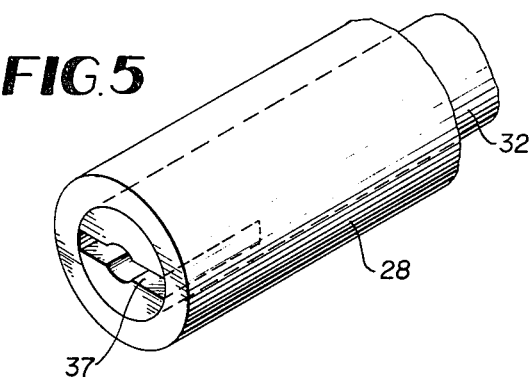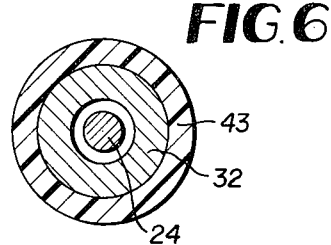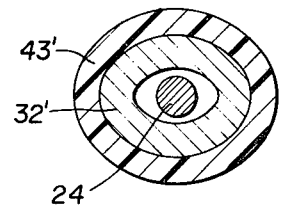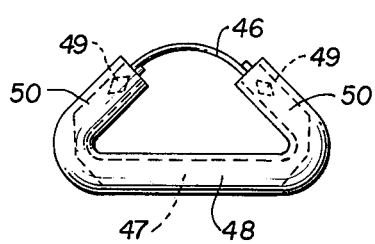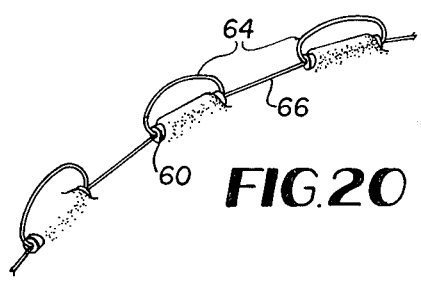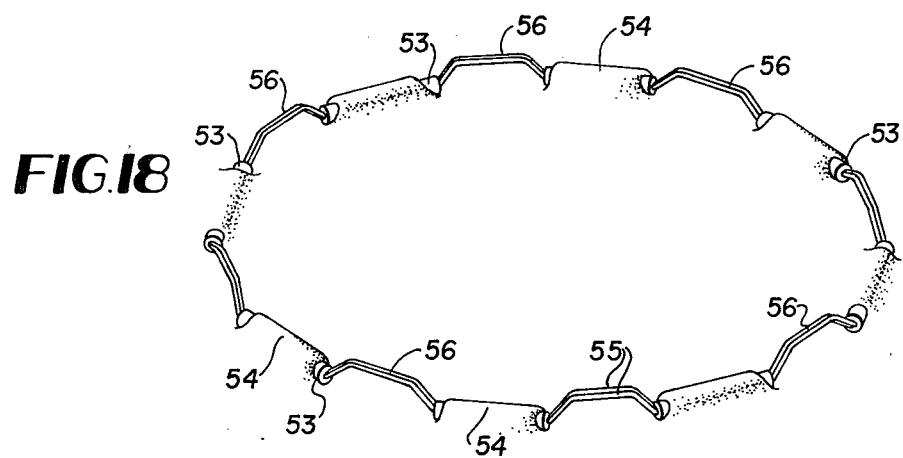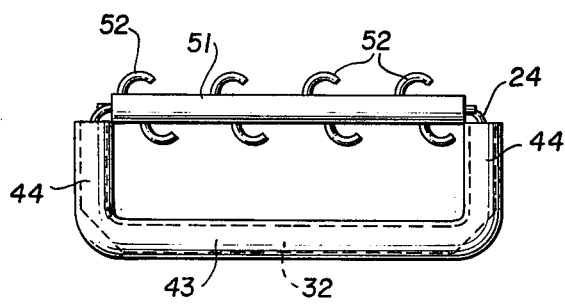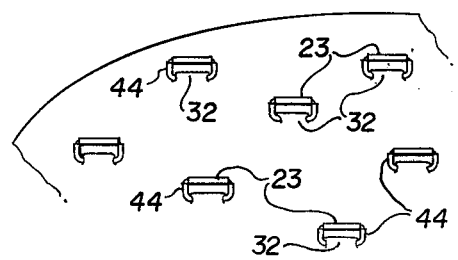

PERMANENTLY IMPLANTED HAIR PIECE ATTACHING MEANS

BACKGROUND OF THE INVENTION

The invention is an improvement on that type of device and method shown in prior U.S. Pat. No. 3,877,570, issued Apr. 15, 1975 to Robert J. Barry. The chief features and advantages of the invention in that patent are retained in the present invention, such as sterility at the time of needle penetration and a single use discardable needle and sterile packaging means.

In the present invention, significant improvement features are embodied. Among these features are the use of a straight needle which may puncture the scalp close and parallel to the bone structure and a trailing flexible preferably transparent inert (Teflon or equivalent) tube within which is placed a preferably stainless steel scalp implant bushing. Much strain is reduced on the edges of the scalp puncture openings by having the rigid bushing implanted beneath the scalp and between the two puncture openings in accordance with the invention. Following implantation, the terminal ends of the bushing and tube are bent upwardly from the scalp and connected with the opposite ends of a tubular lock bar which lies closely above the scalp and parallel to the bushing. The connecting wire is laced through the bushing and lock bar with its ends secured by crimping the tubular lock bar on the wire within it. The structure and procedure entirely eliminates the welding of the prior art and simplifies the entire method while rendering it safer for the subject or receipt.

In accordance with a unique variant, a plurality of bushings are implanted without their ends being upturned from the scalp and the several bushings are interconnected through continuous crimped wire or wires threaded through all of the bushings with the crimped wire portions between the bushings and above the close and parallel to the scalp to facilitate the attachment of hair pieces by various methods. The crimped wire prevents relative movement between bushings and between the wire and bushings. The plural bushings may be implanted in a circular or oval array in the scalp.

Other features and advantages of the invention will become apparent during the course of the following description.

BRIEF DESCRIPTION OF DRAWING FIGURES

FIG. 1 is a perspective view of a sterile package containing the elements which form the subject matter of this invention.

FIG. 2 is an enlarged central vertical longitudinal section through an implant bushing and placement needle assembly according to a main feature of the invention.

FIG. 3 is an enlarged fragmentary longitudinal cross section through a tubular lock bar and associated adjustable bushing attachment wire.

FIG. 4 is a composite side elevational view showing the needle and implant bushing assembly and tubular lock bar prior to installation.

FIG. 5 is an enlarged fragmentary perspective view of one end portion of an implant bushing sub-assembly showing a bushing adjustment or orientation slot.

FIG. 6 is an enlarged transverse vertical section taken through the implant bushing and associated lock bar attaching wire.

FIG. 7 is a similar cross sectional view showing a modification.

FIG. 8 is a plan view of the package invention illustrating the removal of the sterile inner sheath containing the needle and bushing assembly from the outer envelope.

FIG. 9 is a side elevational view of a needle assembly and bushing according to a modification.

FIG. 16 is a side elevational view of an implant bushing and associated parts according to a modification of the invention.

FIG. 17 is a side elevational view showing a modified form of lock bar or top bushing having hooks to facilitate attachment to a hair piece.

FIG. 18 is a perspective view showing another modification of the invention.

FIG. 19 is a fragmentary perspective view of a section of the head showing scalp implanted hair piece attaching units according to the preferred embodiment of the invention.

FIG. 20 is a fragmentary perspective view of a further modification.

DETAILED DESCRIPTION

Figure 10:
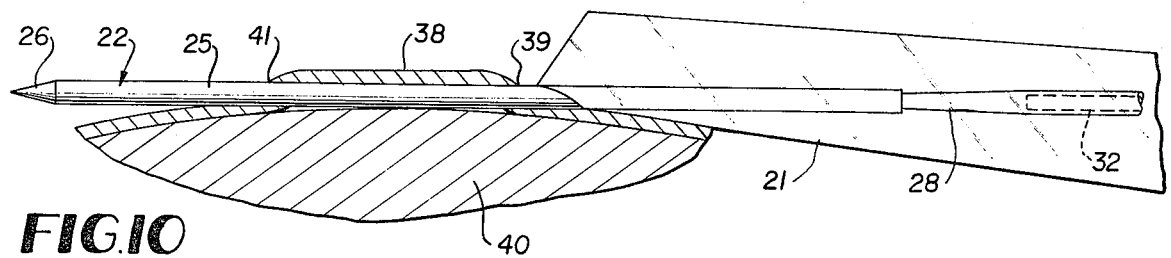
FIG. 10 is an enlarged cross sectional view of the scalp showing the approximately parallel penetration path of the puncturing needle.

Referring to the drawings in detail wherein like numerals designate like parts, and referring initially to FIG. 1, the numeral 20 designates a preferably transparent plastic sealed outer envelope within which is enclosed an inner envelope or sheath 21 which is also sealed and sterile, substantially as disclosed in U.S. Pat. No. 3,877,570. Within the sealed sterile sheath 21 is a needle and implant bushing assembly 22, to be fully described, and within the outer envelope 20 exteriorly of the sheath 21 is a lock bar 23 and a section 24 of wire in assembled relationship, also to be fully described.

Referring to FIGS. 2 and 4, the needle and implant bushing assembly 22 forming a main element of the invention comprises a straight tubular needle body 25, preferably of stainless steel, having a separately formed attached needle point 26 and a gaging mark 27 somewhat rearwardly of the point 26 to facilitate the placement of the implant bushing, to be described, in the scalp. A flexible transparent tube 28 of Teflon or equivalent inert tissue-compatible material has its reduced leading end portion 29 threaded through the tubular needle body 25 with its forward terminal 30 packed rearwardly into the forward end of the needle body as shown in FIG. 2, following which the needle point 26 is secured to the tubular body 25 by known techniques. The tubular body 25 is then clinched at 31 near its rear end to anchor the tube portion 29 therein.

The flexible tube 28 trails the needle body 25 by a predetermined distance and within the rearward portion of the tube 28, a preferably stainless steel straignt tubular implant bushing 32 is snugly arranged and fractionally held with its rear end flush the rear end of the Teflon tube 28. For a reason to be described, the implant bushing 32 has a pair of notches 33 formed in one side thereof in longitudinal alignment and with each notch spaced the same distance from one end of the bushing 32.

The previously-noted tubular lock bar 23 may be coated as at 34, FIG. 3, with Teflon or the like or may be uncoated in some cases. The lock bar is shorter than the implant bushing 32 and is approximately equal to the distance between the two notches 33 of the bushing 32. The lock bar attaching wire 24 of stainless steel or the like is provided in a rather large loop for convenience of manipulation as shown in FIG. 1 with its opposite ends threaded through the tubular lock bar 23 and emerging from the lock bar in opposite directions as indicated at 35.

A needle point protector element 36 is applied over the needle point 26 and is contained in the sterile sheath 21 when the product is packaged. Referring to greatly enlarged FIG. 5, it will be noted that the rearward end of the implant bushing 32 has an orientation slot 37 similar to a screwdriver slot, whereby the bushing can be rotated in the Teflon tube 28 to assure proper placement of the notches 33 which facilitate the bending up of the two end portions of the bushing 32 from the scalp, as will be presently described in connection with FIGS. 10 through 15. The manner of using the invention for implanting the bushing 32 in the scalp 38 is shown in FIGS. 8 and 10 through 15. In FIG. 8, the needle point protector element 36 is dislodged from the needle while the outer envelope 20 is still sealed. The envelope 20 is then cut at its end away from the needle point and the still sealed sheath 21 is removed from the envelope 20 with the rear end of the needle assembly 22 exiting first in the sheath, FIG. 8. As shown in FIG. 10, the needle point is then pushed into the scalp 38 without removal from the sterile sheath 21 by forcing the point 26 through the end of the sheath and into the scalp simultaneously. As the needle advances through the scalp tissue, the sheath 21 is gradually retracted from the needle and bushing assembly until separation of the sheath from the rear end of the assembly takes place at the completion of penetration, FIG. 11. This method assures no contamination of the needle and trailing parts as the same enters the scalp.

The needle assembly being straight rather than curved punctures the scalp 38 at an entrance point 39 and passes nearly parallel to the underlying bone structure 40 before emerging from the scalp at the exit opening 41. While the length of the implanted bushing 32 will vary with skin and skull contours, the implanted center portion of the bushing 32 between the notches 33, FIG. 4, designated B, will be equal to the distance D between the needle point and the indicator line 27. In this way, the location of the scalp exit opening 41 relative to the entrance opening 39 can be gaged or controlled conveniently.

Figure 11:
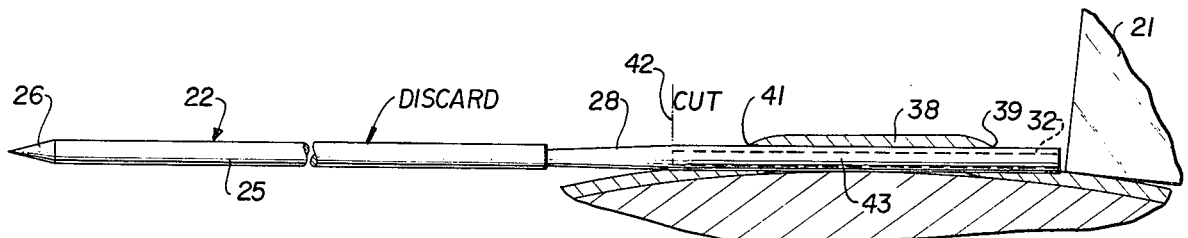
FIG. 11 is a similar view showing the Teflon tube encased bushing in the scalp prior to severing and discarding the needle.

When the intact needle assembly has been drawn through the scalp to the position shown in FIG. 11, the needle body 25 will be well beyond the scalp exit opening 41 and the tube 28 is severed at 42 adjacent the forward end of bushing 32 which is now centered with respect to the two scalp openings 39 and 41 and is fully encased in a sleeve 43 of Teflon or other tissue-compatible plastic, such sleeve having the same length as the bushing 32. The severed needle and trailing portion of the tube 28 ahead of the bushing 32 are discarded. At this time, the bushing 32 may be rotationally adjusted by means of end slot 37 to assure that the bending notches 33 are at the bottom of the bushing relative to the head. The bushing 32 may also be annealed at two points diametrically opposite the notches 33 to further facilitate bending.

Figure 12:
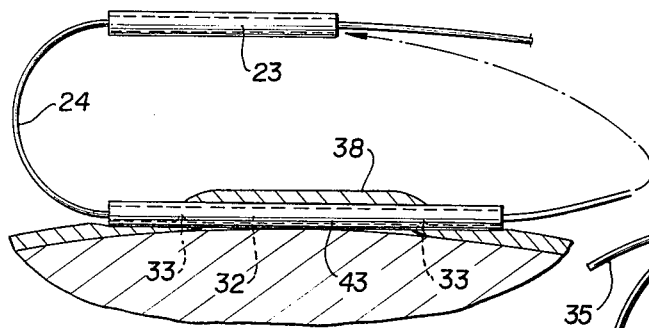
FIG. 12 is a similar view depicting a first step in the attachment of a tubular lock bar to the implanted bushing.
Figure 13:
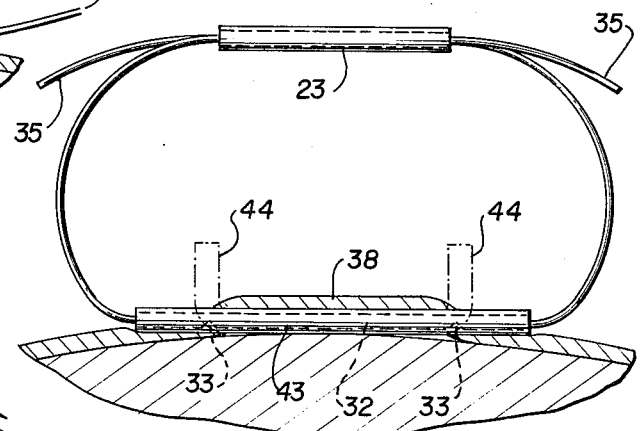
FIG. 13 is a similar view showing the next step in the placement and attachment of the lock bar.
Figure 14:
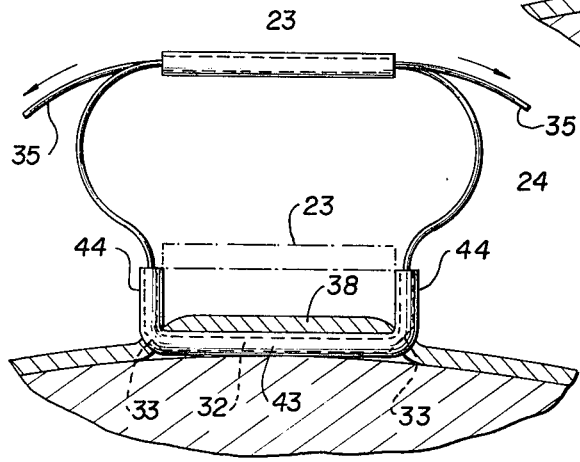
FIGS. 14 and 15 are similar views showing additional and final steps in the attachment of the lock bar to the implanted bushing.

The lock bar 23 and attaching wire 24, FIG. 12, are now withdrawn from the envelope 20 and one end of the wire is threaded through the straight bushing 32, FIG. 12, and returned through the tubular lock bar 23, FIG. 13, to form a closed loop with the two tubular elements 23 and 32 with the wire ends 35 extending beyond the ends of the lock bar. At this time, the end portions of the implanted bushing 32 and enclosing sleeve 43 are bent upwardly at right angles to the bushing axis as indicated in broken lines at 44 in FIG. 13 and in full lines in FIG. 14, the notches 33 greatly facilitating such bending. The end portions 35 of the wire 24 are then grasped and pulled outwardly from opposite ends of the lock bar 23, FIG. 14, to gradually shorten the wire loop and draw the lock bar downwardly to a final position at the tops of the bent-up arms or extensions 44. At this final position, FIG. 15, the lock bar 23 is close to the implanted bushing 32 and parallel thereto and substantially at right angles to the short upstanding bushing arms 44, the bushing and its sleeve 43 now having assumed a short U-configuration. At this point, the wire ends 35, after being flexed a few times, will break off and the lock bar 23 is clinched near its opposite ends at 45 to permanently secure it to the wire loop 24. In contrast to the arrangement in U.S. Pat. No. 3,877,570, all welding has been eliminated and the fastening is purely mechanical. The straight lock bars 23 lie close to the scalp and the straight scalp implanted bushing 32 reduces the strain at the edges of the scalp openings 39 and 41 in comparison to the prior art where oval loops are implanted in the scalp. The resulting construction is simpler and the method of installation is simpler and safer than the prior art.

After a sufficient number of bushings 32 are implanted in the scalp in spaced relation with the lock bars 23 attached, hair pieces can be secured to the lock bars 23 by a number of known methods.

FIG. 16 shows a modification of the invention wherein the tubular lock bar 23 is eliminated and instead thereof a wire 46 is passed through the implanted bushing 47 and its Teflon sleeve 48 and secured by clinching at 49 near opposite ends of the bushing structure. In this embodiment, the opposite end portions 50 of the implanted bushing are bent into upwardly converging relationship to assume angles of about 45° to the straight scalp implanted section. The comparatively short section 46 of wire between the extensions 50 is then used for the attachment of a hair piece. The implanting procedure for the stainless steel bushing 47 is the same as described previously for the bushing 32.

FIG. 17 shows a further modification of the invention wherein the tubular lock bar 51 is provided with a plurality of randomly arranged resilient hooks 52 which preferably face in one direction. These hooks may be welded to the stainless steel lock bar 51. They are used as a means for attaching a membrane, not shown, containing hair in a manner for easy removal, and to provide a fail-safe breakaway arrangement should be hair piece be pulled abruptly, thus avoiding injury to the scalp. The hooks 52 will preferably have an elastic memory and will return to their normal shapes following a severe pull. The use of the hooks 52 does not preclude tying tufts of hair in the ordinary manner, if preferred.

FIG. 7 shows a slight variant of the invention in comparison to FIG. 6 which is a cross sectional view taken through the implanted bushing 32, its external sleeve 43 and the attaching wire 24. FIG. 7 simply shows that the bushing 32' may in some cases be flattened to an oval configuration with its Teflon sleeve 43' to bring the assemblage even closer to the skull.

FIG. 18 shows a modification of the invention wherein a number of Teflon covered straight bushings 53 are implanted in a space array in the scalp 54 by the same method depicted in FIGS. 10 through 12. In lieu of bending the bushing arms 44 upwardly from the scalp as in FIG. 15, and employing a separate wire loop 24 for each implant, the straight shorter bushings 53 are installed and preferably a double wire 55 is threaded serially through all of the implanted bushings 53 with its ends attached in a conventional way to make the wire endless. After such threading, the wire is crimped as at 56 uniformly between each pair of bushings 53 and the straight sections of these crimps 56 are parallel to the bushings and only slightly elevated from the scalp so that the invention possesses essentially the same advantages over the prior art as were described in the prior embodiment. Additionally, the crimped portions 56 prevent relative longitudinal movement between the wire and bushings 53 and thereby also prevent movement of the bushings in the scalp. A hair piece is attached to the elevated crimped wire portions by any desired technique. The array of bushings 53 in the scalp may be variously shaped, as circular or oval.

In addition to the previously stated advantages of the invention, it should be apparent that the use of the stainless steel implant bushing 32 permits the use of a very small diameter wire (0.005 inch or less) without any danger of cutting through the Teflon covering.

Figure 15:
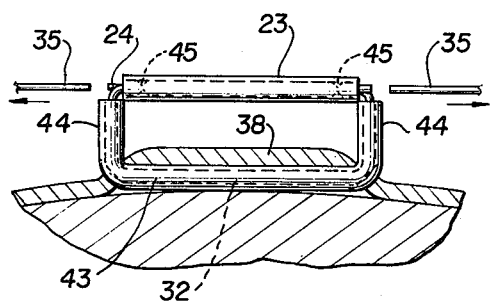

The invention also possesses a safety break-away feature in that the wire loop 24, FIG. 15, is frictionally secured rather than being welded.

The length of the needle body or shank visible through the plastic sheath 21 allows holding and manipulating by the fingers rather than by forceps without loss of sterility and making the implant procedure more responsive to a sensitive touch by the technician.

Since the Teflon tubing 28, FIG. 2, extends well toward the front of the needle body 25, even if the needle should pull away from the tubing under tension, a sufficient length of the Teflon tubing will project from the exit opening 41 to allow grasping for final pulling of the bushing into position.

In case of a broken wire, the ends of the implant bushing can be straightened and a new wire threaded therethrough. If the end portion of a bushing should break off, it will still serve its intended purpose being confined in the Teflon sleeve, which purpose is to protect the sleeve from being cut by the very small wire. Therefore, many repairs can be made without additional surgery.

FIGS. 9 and 20 depict a further modification in which a continuous wire system is employed somewhat similar to FIG. 18, but a partial application or system may be utilized in FIG. 20 instead of the closed loop arrangement of FIG. 18. Referring to FIG. 9, a needle and bushing assembly 22' having a straight tubular needle body 25' and a slender elongated point 26' is provided. A trailing Teflon tube 28', similar to the described tube 28, is attached preferably as shown in FIG. 2. A stainless steel implant bushing 60 within the trailing tube 28' has a pair of spaced annular enlargements 62 which prevent involuntary displacement of the bushing. The distance X between the enlargements 62 equals the distance X on the needle point 26' so that the previously described indicator mark or groove 27 on the needle is not necessary. The arrangement in FIG. 9 is preferred. The purpose of the arrangement is the same as previously described for controlling the extent of scalp penetration between openings such as 39 and 41. The assembly 22' has a sterile sheath and packaging, as previously described, and is placed in the scalp substantially as described in connection with FIGS. 10 and 11.

As shown in FIG. 20, any number of the scalp implanted straight bushings 60 may be connected with a bridging wire 66 passed therethrough axially and this wire will be supplied on a separate spool for convenience. The same continuous bridging wire 66 is looped at 64 above the scalp and above each implanted bushing 60, and the several loops 64 provide ready hairpiece anchoring means. The bridging wire 66 may be tight or loose, as desired. The arrangement is simple as a single section of wire joins the several bushings 60 and forms the hairpiece attachment loops, as stated.

The advantages of the invention over the prior art should now be apparent to those skilled in the art.

It is to be understood that the forms of the invention herewith shown and described are to be taken as preferred examples of the same, and that various changes in the shape, size and arrangement of parts may be resorted to, without departing from the spirit of the invention or scope of the subjoined claims.

I claim:

1. A scalp implant for attaching a hair piece to the scalp comprising a needle adapted to puncture the scalp generally parallel to the surface of the skull and thereby form entrance and exit puncture openings in the scalp, a trailing tube of tissue-compatible material attached to the needle and adapted to be severed therefrom after the needle has drawn said tube into implanted relationship with the scalp with opposite ends of the tube extending substantially equidistantly outside of the scalp beyond said entrance and exit puncture openings, a metallic sleeve bushing contained bodily within said tube and having a central main portion substantially equal in length to the distance between said entrance and exit puncture openings and comparatively short end portions adapted to be bent upwardly approximately at right angles to said central main portion to thereby project outwardly of and above the scalp, said comparatively short end portions of the bushing being substantially equal in length to corresponding end portions of said tube within which said metallic sleeve bushing is contained, and said tube end protions being bendable with said short end portions of the metallic bushing, a substantially straight tubular lock bar formed separately from and substantially equal in length to said central main portion of said metallic bushing, and a lock bar attaching wire threadable through said bushing and said lock bar and adapted when tightened and secured to position said lock bar between the tops of the comparatively short upwardly bent bushing and tube end portions with the lock bar outside of the scalp and substantially parallel to said central main portion of the bushing and spaced therefrom, whereby said implant is in the form of a closed substantially rectangular loop.

2. A scalp implant for attaching hair pieces to the head as defined by claim 1, and said metallic bushing being notched at the opposite ends of said central main portion to facilitate the upward bending of said comparatively short end portions of the bushing.

3. A scalp implant for attaching hair pieces to the head as defined by claim 2, and said metallic bushing having a single pair of notches on one side thereof and both notches being aligned circumferentially of said metallic bushing.

4. A scalp implant for attaching hair pieces to the head as defined by claim 1, and said needle comprising a substantially straight needle arranged substantially coaxially with said trailing tube prior to the installation of said scalp implant.

5. A scalp implant for attaching hair pieces to the head as defined by claim 1, and tubular lock bar comprising a metallic element, and said lock bar attaching wire comprising an elongated single section flexible wire threaded through said bushing and having its opposite ends extending beyond opposite ends of the bushing and threaded through said lock bar in opposite directions with the opposite wire ends projecting beyond opposite ends of the lock bar, whereby pulling on such wire ends will draw the lock bar into its use position between the tops of the upwardly bent bushing and tube end portions.

6. A scalp implant for attaching hair pieces to the head as defined by claim 1, and said tubular lock bar fixed in its assembled relationship to said attaching wire by being clinched to the wire near opposite ends of said lock bar.

7. A scalp implant for attaching hair pieces to the head as defined by claim 5, and said lock bar being clinched on two strands of said attaching wire extending therethrough to fix the lock bar in its use position on said scalp implant.

* * * * *